United States Patent
Tamura et al.

(10) Patent No.: US 9,517,043 B2
(45) Date of Patent: Dec. 13, 2016

(54) MULTI-SOURCE RADIATION GENERATOR AND RADIOGRAPHY SYSTEM

(71) Applicant: CANON KABUSHIKI KAISHA, Tokyo (JP)

(72) Inventors: Miki Tamura, Kawasaki (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 164 days.

(21) Appl. No.: 14/335,650

(22) Filed: Jul. 18, 2014

(65) Prior Publication Data

US 2015/0030119 A1 Jan. 29, 2015

(30) Foreign Application Priority Data

Jul. 23, 2013 (JP) .................. 2013-152180

(51) Int. Cl.
| | |
|---|---|
| H05G 1/70 | (2006.01) |
| A61B 6/00 | (2006.01) |
| A61B 6/02 | (2006.01) |
| H01J 35/04 | (2006.01) |
| H01J 35/08 | (2006.01) |
| H01J 35/16 | (2006.01) |
| H01J 35/18 | (2006.01) |
| H05G 1/08 | (2006.01) |

(52) U.S. Cl.
CPC .............. *A61B 6/542* (2013.01); *A61B 6/025* (2013.01); *A61B 6/4007* (2013.01); *H01J 35/045* (2013.01); *H01J 35/08* (2013.01); *H01J 35/16* (2013.01); *H01J 35/18* (2013.01); *H05G 1/085* (2013.01); *H05G 1/70* (2013.01); *H01J 2235/068* (2013.01); *H01J 2235/087* (2013.01); *H01J 2235/168* (2013.01)

(58) Field of Classification Search
CPC ....... A61B 6/025; A61B 6/542; G01N 23/046; H01J 35/14; H01J 35/30; H01J 35/045; H01J 2235/068; H05G 1/00; H05G 1/02; H05G 1/30; H05G 1/32; H05G 1/34; H05G 1/38; H05G 1/46; H05G 1/56; H05G 1/58
USPC .................. 378/21, 22, 62, 92, 108–115, 134
See application file for complete search history.

(56) References Cited

U.S. PATENT DOCUMENTS

| | | | |
|---|---|---|---|
| 7,978,816 B2* | 7/2011 | Matsuura | A61B 6/032 378/62 |
| 8,094,773 B2 | 1/2012 | Boese et al. | |
| 8,447,011 B2* | 5/2013 | Ohta | A61B 6/00 378/62 |
| 2010/0124311 A1 | 5/2010 | Enomoto et al. | |
| 2013/0208852 A1 | 8/2013 | Koishi | |

* cited by examiner

*Primary Examiner* — Jurie Yun
(74) *Attorney, Agent, or Firm* — Canon USA Inc. IP Division (57) ABSTRACT

A multi-source radiation generator in which plural radiation sources are arranged in series includes a control unit that controls a dose of radiation emitted from each of the radiation sources depending on positions of the radiation sources, and reduces variation in a radiation dose resulting from differences in positions of the radiation sources by changing an irradiation time, an anodic current value of each of the radiation sources depending on a distance from each of the radiation sources to a subject.

16 Claims, 9 Drawing Sheets

MULTI-SOURCE RADIATION GENERATOR AND RADIOGRAPHY SYSTEM

BACKGROUND OF THE INVENTION

Field of the Invention

The present invention relates to a multi-source radiation generator applicable to, for example, non-destructive X-ray radiography in the field of medical and industrial equipment, and relates also to a radiographic imaging system using the multi-source radiation generator.

Description of the Related Art

Recently, in medical inspections, such as mammography, tomosynthesis imaging is performed as a technique to obtain information in a depth direction of a sample. In tomosynthesis imaging, the sample is irradiated with radiation from a radiation generator which moves over a limited arc and emits the radiation at plural angles, and the sample is imaged by obtaining plural images. The obtained plural images are reconstructed using specific algorithms to form a tomographic image.

More specifically, in conventional tomosynthesis imaging, typically, radiographic imaging is performed by applying radiation to the sample while a radiation tube is moved in a predetermined angle range (±7.5° to ±25°) with respect to the sample. However, there have been the following problems: an artifact may be produced in an image because the radiation tube is moved at the time of radiographic imaging of the sample; and prolonged radiographing time is required because a mechanical movement takes time. Further, there has been a possibility that a subject feels fear at the movement of the radiation tube.

U.S. Pat. No. 8,094,773 discloses a technique to obtain a three-dimensional X-ray radiographic image by performing tomosynthesis imaging using plural X-ray sources that are arranged in series.

A multi-source radiation tube in which plural radiation sources are arranged in series is advantageous in that the size of the entire apparatus may be reduced and that the multi-source radiation tube may be manufactured in a simplified and affordable manner. An integrally formed radiation tube is especially advantageous in manufacture.

However, since a distance between the radiation source and the subject varies depending on the position of the radiation source, there is variation in an exposure dose. For this reason, there has been a problem that, there is variation in the exposure dose in the obtained plural images and, therefore, a tomographic image obtained by reconstructing these images is not necessarily favorable.

SUMMARY OF THE INVENTION

The present invention provides a radiation generator and a radiographic imaging system which improve image quality of imaging by, among other factors, reducing variation in an exposure dose resulting from differences in positions of radiation sources.

A multi-source radiation generator (hereafter, "radiation generator") of the present invention includes: electron sources configured to emit electrons, radiation sources arranged in series and provided with targets configured to generate radiation when electrons emitted from the electron sources are applied thereto, and a control unit configured to control a dose of radiation emitted from the radiation sources depending on positions of the radiation sources.

Further features of the present invention will become apparent from the following description of exemplary embodiments with reference to the attached drawings.

DESCRIPTION OF THE EMBODIMENTS

A first embodiment is directed a multi-source radiation generator and a technique to control a radiation dose by controlling radiating time (radiographing time) of each radiation source. A second embodiment is directed a technique to control a radiation dose by controlling a current amount of each radiation source. A third embodiment is directed to a radiographic imaging system provided with the radiation generator described in the first and/or second embodiment. Although X-ray radiation is used as an example of radiation in the present embodiment, a neutron beam or a proton beam may also be used as the source of radiation.

First Embodiment

Figure 1A:
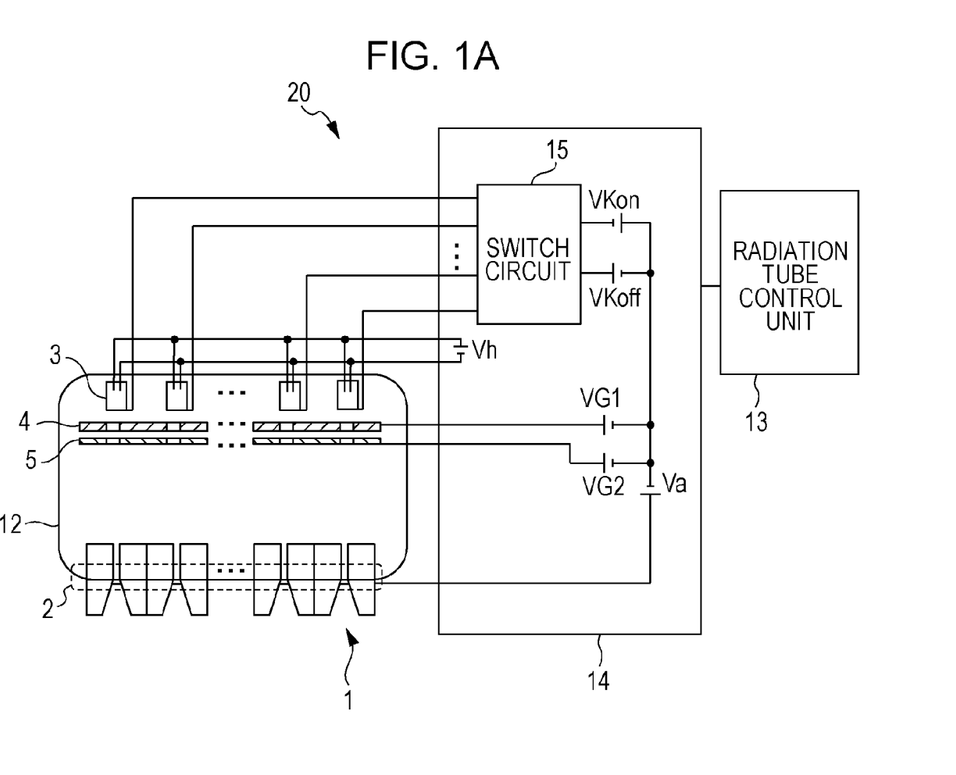
FIG. 1A is a schematic diagram illustrating a configuration of an exemplary multi-source radiation generator according to a first embodiment.
Figure 1B:
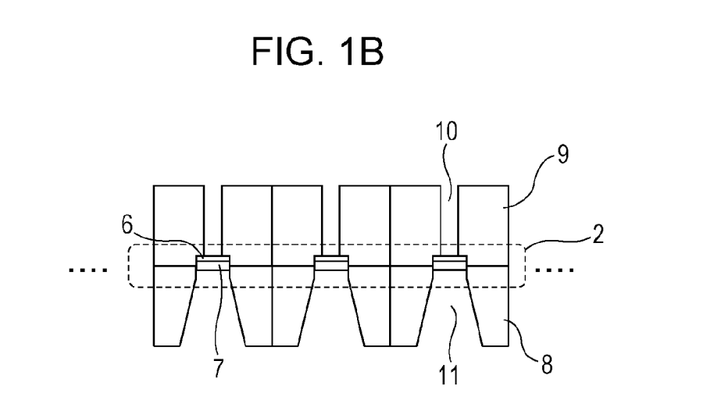
FIG. 1B is an enlarged view of a part of the multi-source radiation generator illustrated in FIG. 1A.

FIG. 1A is a schematic diagram illustrating an exemplary radiation generator of the present embodiment. FIG. 1B is an enlarged view of a part of a radiation source illustrated in FIG. 1A.

In FIG. 1A, a radiation generator 20 includes a radiation tube 1, a radiation tube control unit 13 (radiation controller) and a voltage control unit 14 (voltage controller).

The radiation tube 1 includes plural electron sources 3 that emit electrons, a radiation source array 2 that generates radiation when electrons emitted from the electron sources are applied thereto, and an outer case 12 (housing). The radiation source array 2 includes plural radiation sources that are arranged in series at predetermined intervals. Each of the radiation sources 2 includes a target 6 and a substrate 7 that supports the target 6. When the electrons emitted from an electron source 3 enter a target 6, radiation is generated therein. The radiation generated at the target 6 passes through the substrate 7 and is then emitted outside the radiation tube 1.

The inside of the radiation tube 1 is maintained under vacuum. In one embodiment, it is necessary that the degree of vacuum inside the radiation tube 1 is about $10^{-4}$ to $10^{-8}$ Pa. An unillustrated "getter" may be provided inside the radiation tube 1 to maintain the necessary degree of vacuum.

As the electron source 3, a tungsten filament, a hot cathode, such as an impregnated cathode, or a cold cathode, such as a carbon nanotube, may be used. An extraction electrode 4 and a convergence electrode 5 may be provided between the electron source 3 and the target 6. An electric field formed by the extraction electrode 4 causes the electron source 3 to emit electrons. The emitted electrons are converged at the convergence electrode 5 and enter the target 6, whereby radiation is generated.

The target 6 is disposed on a surface of the substrate 7 on the side of the electron source 3. The target 6 may be desirably made of a material that has high melting point and high radiation generation efficiency. For example, tungsten, tantalum, molybdenum and alloys thereof may be used. A suitable thickness of the target 6 is 1 to 20 μm.

The substrate 7 is desirably made of a material that has enough strength to support the target 6, is not likely to absorb the radiation generated at the target 6, and has high thermal conductivity so as to quickly radiate the heat generated at the target 6. For example, diamond, silicon carbide and aluminum nitride may be used. A suitable thickness of the substrate 7 is 0.05 to 10 mm.

Shielding members 8 and 9 may be provided near the target 6 and the substrate 7. The shielding members 8 and 9 shield unnecessary components (stray radiation) of the radiation emitted from the target 6. Here, the shielding member 9 disposed on the side facing toward the electron source 3 with respect to the target 6 is defined as a rear shielding member 9, and the shielding member 8 disposed on the opposite side of the electron source 3 via the target 6 is defined as a front shielding member 8.

The electrons emitted from the electron source 3 pass through a through hole 10 of the rear shielding member 9 and are made to strike on the target 6. At this time, an unnecessary component of the radiation scattered toward the electron source 3 from the target 6 is shielded by the rear shielding member 9. The radiation which has passed through the target 6 and the substrate 7 passes through an opening 11 of the front shielding member 8. Here, since the unnecessary component of the radiation is shielded by the front shielding member 8, a radiating angle of the radiation is restricted. The shielding members 8 and 9 are desirably made of materials that have high radiation absorptivity and high thermal conductivity. For example, metallic materials, such as tungsten, tantalum and copper, may be used for shielding members 8 and 9. Although the shielding members of each radiation source are illustrated as separated members in FIGS. 1A and 1B, it is desirable that the shielding members are formed integrally with each other during manufacture.

The radiation tube control unit 13 controls an operation of the radiation tube 1. In accordance with a control signal from the radiation tube control unit 13, a predetermined voltage is applied to each part of the radiation tube 1 at predetermined timing by the voltage control unit 14.

Figure 2:
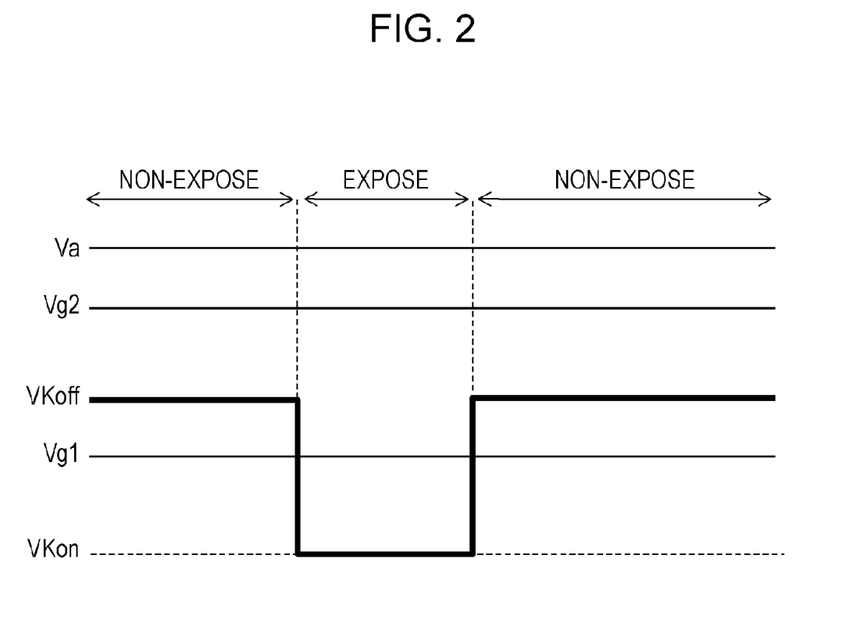
FIG. 2 is an explanatory graph illustrating an exemplary method of applying a voltage to the radiation generator according to the first embodiment.

A method for driving the multi-source radiation generator will be described with reference to the block diagrams of FIGS. 1A and 1B, and the timing diagram of FIG. 2. First, as shown in FIG. 2, at a time of non-exposure (standby), a heater voltage (Vh) is applied to a filament of the electron source 3 (shown in FIG. 1A). A voltage potential of the radiation source array 2 is set to anode potential (Va), a voltage potential of the extraction electrode 4 is set to an extraction potential (Vg1), and a voltage potential of the convergence electrode 5 is set to convergence potential (Vg2). A voltage potential of the electron source 3 is set to cutoff potential VKoff. Since VKoff is higher than Vg1, electron emission from the electron source 3 is reduced and radiation is not emitted. At the time of exposure, by setting the voltage potential of the electron source 3 to an operation voltage VKon which is lower than Vg1, electrons are emitted from the electron source 3, and the emitted electrons are applied to each radiation source of the radiation source array 2. In the tomosynthesis imaging, a radiation source which performs exposure is sequentially selected using a switch circuit 15. The potential of the electron source 3 corresponding to the selected radiation source is set to VKon, and the potential of the electron source 3 corresponding to a radiation source that is not selected is set to VKoff. That is, radiation is sequentially emitted from the radiation sources at a predetermined time and frequency by applying operation voltage VKon sequentially from an electron source corresponding to a radiation source disposed at one end portion to an electron source corresponding to a radiation source disposed at the other end portion. Potential of the current that flows through the target (hereafter, an anodic current) may be changed by changing the potential of VKon.

In non-tomosynthesis imaging, a still image may be taken by driving only a specific radiation source located at a desired position (e.g., at the center) of the radiation source array 2 without performing sequential application of Vkon as described above.

Switching between exposure and non-exposure may be performed by switching the extraction potential (Vg1) to any of cutoff potential and operation potential with the potential of the electron source 3 being fixed.

Next, a method for controlling the radiation generator 20 performed in the radiation tube control unit 13 will be described with reference to FIGS. 3 to 5.

Figure 3:
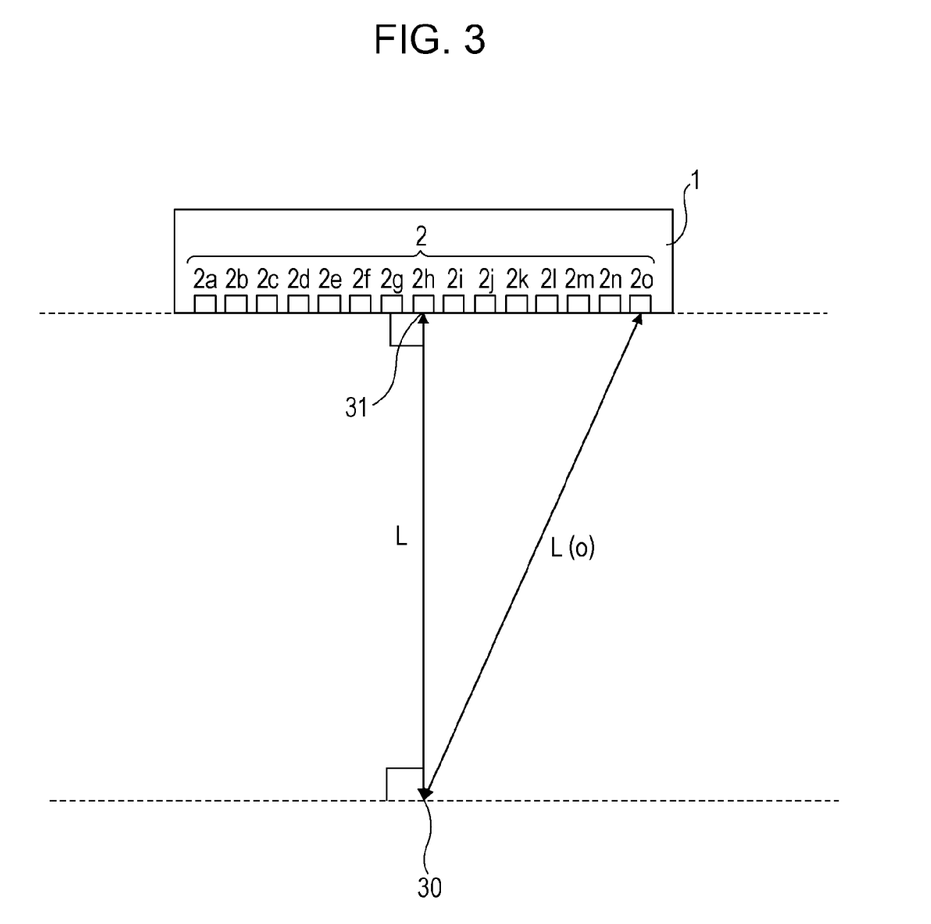
FIG. 3 is an explanatory view illustrating a method for controlling the radiation generator according to the first embodiment.

FIG. 3 is a diagram illustrating a positional relationship between a radiation source array 2 and an arbitrary point 30. The arbitrary point 30 is located outside the radiation tube 1 at a predetermined position facing the radiation source array 2. The arbitrary point 30 may correspond to a focusing point on an imaging plane, for example, a plane where a radiation detector is located during imaging. The radiation source array 2 is constituted by, for example, a predetermined number (15 in the drawing) of radiation sources 2a to 2o.

Figure 4:
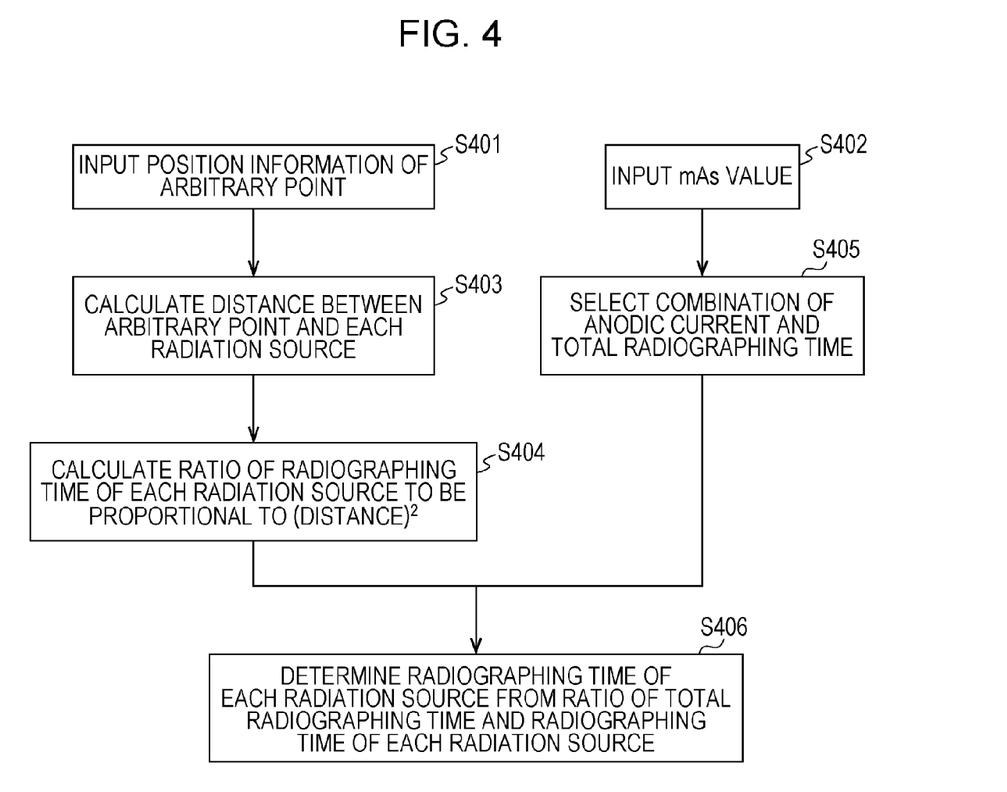
FIG. 4 is a flowchart illustrating a process or method for controlling the radiation generator according to the first embodiment.

FIG. 4 is a flowchart illustrating processes of a method for controlling the multi-source radiation generator. First, position information of the arbitrary point 30 (S401) and a radiographic milliamperage second mAs value (S402) are input. The mAs value is a product of the anodic current in milli-Amps (mA) and radiographing exposure time in seconds (s). Here, position information is, for example, three-dimensional coordinates (X, Y, Z) of the arbitrary point 30. When the coordinates of the arbitrary point 30 are input, at S403, "a distance between the arbitrary point 30 and each radiation source" is calculated in accordance with previously input coordinates of each of the radiation sources 2a to 2o. Next, at S404, a ratio of the radiographing time for each radiation source is calculated to be proportional to a square of "the distance between the arbitrary point 30 and each radiation source." Since an exposure dose is inversely proportional to the square of the source-to-image distance (SID), variation in the exposure dose of some radiation sources may be reduced by setting the radiographing time to be proportional to the square of "the distance between the arbitrary point 30 and each radiation source." An appropriate combination of the anodic current and the total radiographing time is selected at S405 on the basis of the input radiographic mAs value. Then, at S406, radiographing time for each radiation source is determined on the basis of the ratio of the selected total radiographing time and the radiographing time of each radiation source.

The arbitrary point 30 may also be an arbitrary point on a perpendicular line that passes through the central position 31 of the radiation source array 2 as illustrated in FIG. 3. In this case, a distance L between the central position 31 of the radiation source array 2 and the arbitrary point 30 may be input as the position information. The distance between the arbitrary point 30 and each radiation source 2 may be obtained based on basic trigonometry from the distance L (distance from point 30 to center of central radiation source 2h and the distance between the central position 31 and each radiation source to the left or right of the central position 31.

Figure 5:
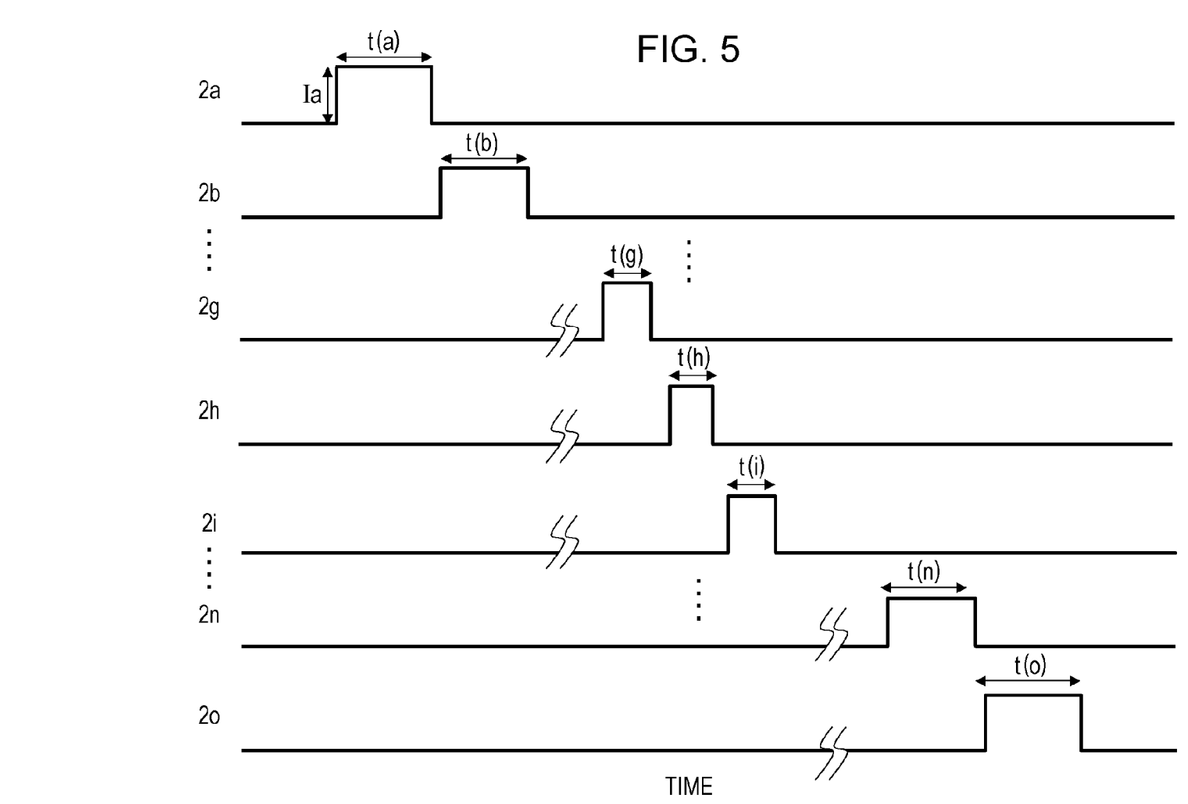
FIG. 5 is a time diagram illustrating a method for driving the radiation generator according to the first embodiment.

FIG. 5 is a schematic diagram illustrating a method for driving each radiation source of FIG. 3, and illustrating an exemplary case in which the radiation sources 2a to 2o are driven sequentially. For each of the radiation sources 2a to 2o, the same amount of anodic current Ia and different lengths radiographing times t(a) to t(o) are set. The length (period) of radiographing times t(a) to t(o) are determined by the method illustrated in the flowchart of FIG. 4. In the present embodiment, since "the distance between the arbitrary point 30 and each radiation source" becomes longer as the position of the radiation source approaches the end portions of the multi-source radiation generator, the radiographing time for the radiation sources located on the end portions is set to be longer that the radiographing time for the radiation sources located directly facing the arbitrary point 30. For example, as illustrated in FIG. 5, the length or period of time for exposing a subject (radiographing time) with radiation source 2h is shorter than the length of time for exposing the subject with each of the radiation sources 2i, 2j, 2k, 2l, 2m, 2m and 2m.

As described above, variation in the exposure dose at the arbitrary point 30 may be reduced by changing the radiographing time of each radiation source depending on the distance between the arbitrary point 30 and each radiation source.

Second Embodiment

The configuration of the radiation generator according to the present embodiment is the same as that of the first embodiment.

Figure 6:
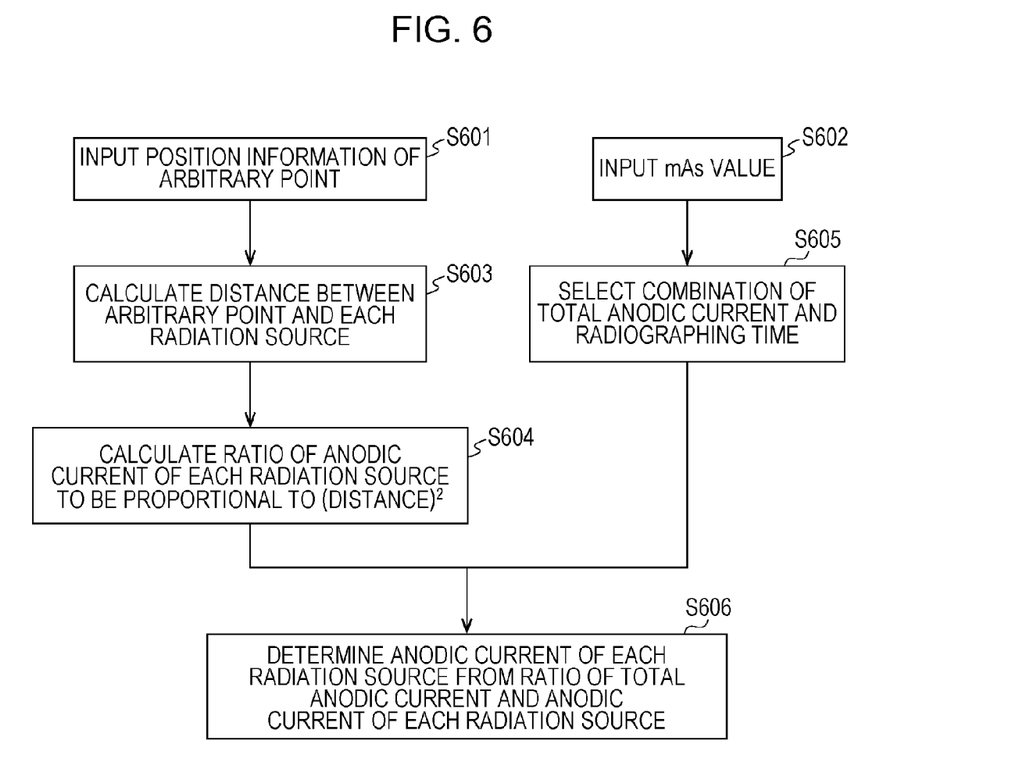
FIG. 6 is a flowchart illustrating another process or method for controlling a radiation generator according to a second embodiment.

FIG. 6 is a flowchart illustrating a method for controlling the multi-source radiation generator according to the second embodiment. First, position information of each individual radiation source (S601) and a radiographic mAs value of an arbitrary point 30 (S602) are input in the same manner as in the first embodiment. Next, at S603, "a distance between the arbitrary point 30 and each radiation source" is calculated. Next, at S604, a ratio of anodic current of each radiation source is calculated to be proportional to the square of "the distance between the arbitrary point 30 and each radiation source." Since an exposure dose is inversely proportional to the square of the distance, variation in the exposure dose may be reduced by setting the anodic current to be proportional to the square of the "distance between the arbitrary point 30 and each radiation source." Accordingly, at S605, an appropriate combination of the total anodic current for all radiation sources and the radiographing time is selected on the basis of the input radiographic mAs value. The anodic current of each radiation source is determined (S606) on the basis of the ratio of the selected total anodic current and the anodic current of each radiation source.

Figure 7:
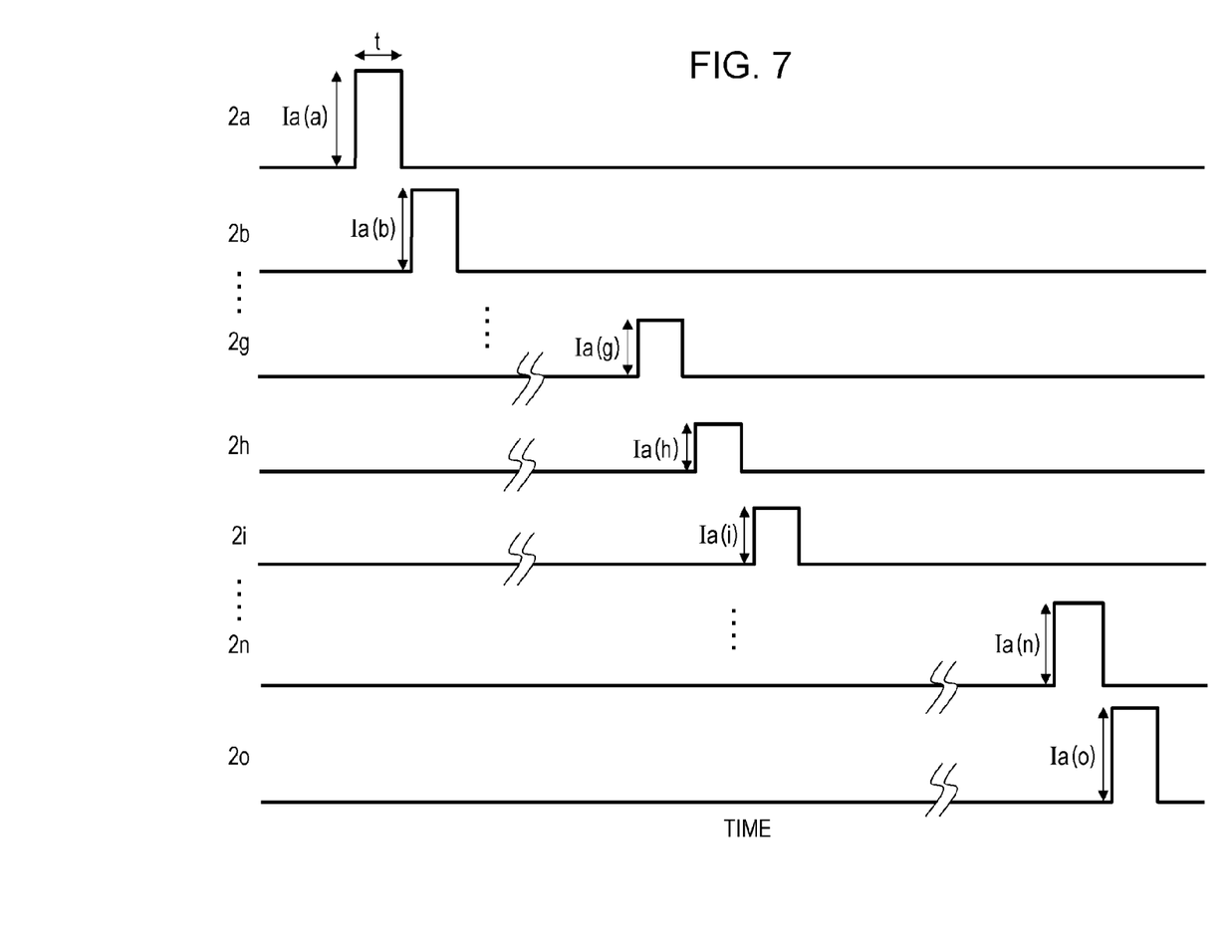
FIG. 7 is a time diagram illustrating another method for driving the radiation generator according to the second embodiment.

FIG. 7 is a schematic diagram illustrating a method for driving the radiation source and illustrating an exemplary case in which the radiation sources 2a to 2o illustrated in FIG. 3 are driven sequentially with the same duration of radiographing time, but with different levels of anodic current for each radiation source. Further, an example in which the arbitrary point 30 in FIG. 3 is input is illustrated. For each of the radiation sources 2a to 2o, the same radiographing time t and different levels of anodic currents Ia(a) to Ia(o) are set. The anodic currents Ia(a) to Ia(o) are determined on the basis of the flowchart of FIG. 6. In the present embodiment, since "the distance between the arbitrary point 30 and each radiation source" becomes longer as the radiation source approaches the end portions of the multi-radiation source, the level or amount of anodic current for a radiation source located in the end portions is set to be higher.

In this manner, as described above, variation in the exposure dose at the arbitrary point 30 may be reduced by changing the anodic current of each radiation source depending on the distance between the arbitrary point 30 and each radiation source.

As described above, according to the first and the second embodiments, a radiation generator with reduced variation in an exposure dose resulting from differences in positions of radiation sources may be provided.

Third Embodiment

Figure 8:
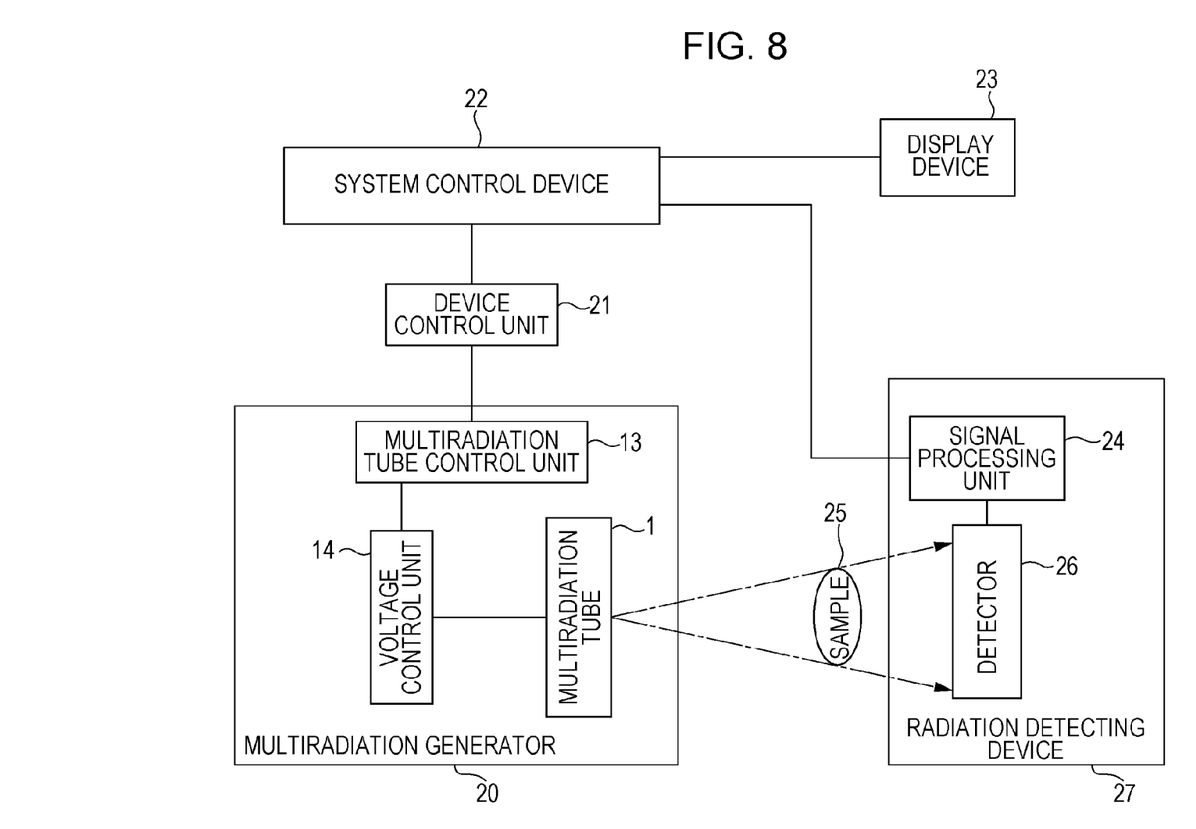
FIG. 8 is a block diagram illustrating an exemplary configuration of a radiographic imaging system according to a third embodiment.

FIG. 8 is a block diagram of an exemplary configuration of a radiographic imaging system in which the radiation generator 20 of the present invention is used. A system control device 22, such as a modality's computer, controls the radiation generator 20 and a radiation detecting device 27 in a coordinated manner. A device control unit 21 outputs various kinds of control signals to the radiation tube control unit 13 under the control of the system control device 22. An emission state of radiation emitted from the radiation tube 1 is controlled by the control signals. The radiation emitted from the radiation tube 1 passes through a sample 25 (subject) and is detected by a radiation detector 26. The radiation detecting device 27 converts the detected radiation into image signals, and outputs the image signals to a signal processing unit 24. The signal processing unit 24 carries out predetermined signal processing to the image signals under the control of the system control unit 22, and outputs the processed image signals to the system control unit 22. The system control unit 22 outputs display signals to a display device 23 so that an image is displayed on the display device 23 in accordance with the processed image signals. The display device 23 displays the image in accordance with the display signal on a screen as a radiographed image of the sample 25.

The radiographic imaging system has a tomosynthesis imaging mode and a non-tomosynthesis imaging mode, which are switched by an operation of an operator.

Next, the tomosynthesis imaging using the radiographic imaging system of the present embodiment will be described with reference to FIG. 9. In the tomosynthesis imaging, the sample 25 is irradiated with radiation emitted from plural radiation sources 2a to 2o sequentially at different angles. The radiation which has passed through the sample 25 is sequentially detected by the detector 26 and images corresponding to the exposure by each of the radiation sources 2a to 2o are taken. The plural radiographed images are reconstructed in the signal processing unit 24 (shown in FIG. 8) using specific algorithms and a tomographic image of the sample is formed.

Figure 9:
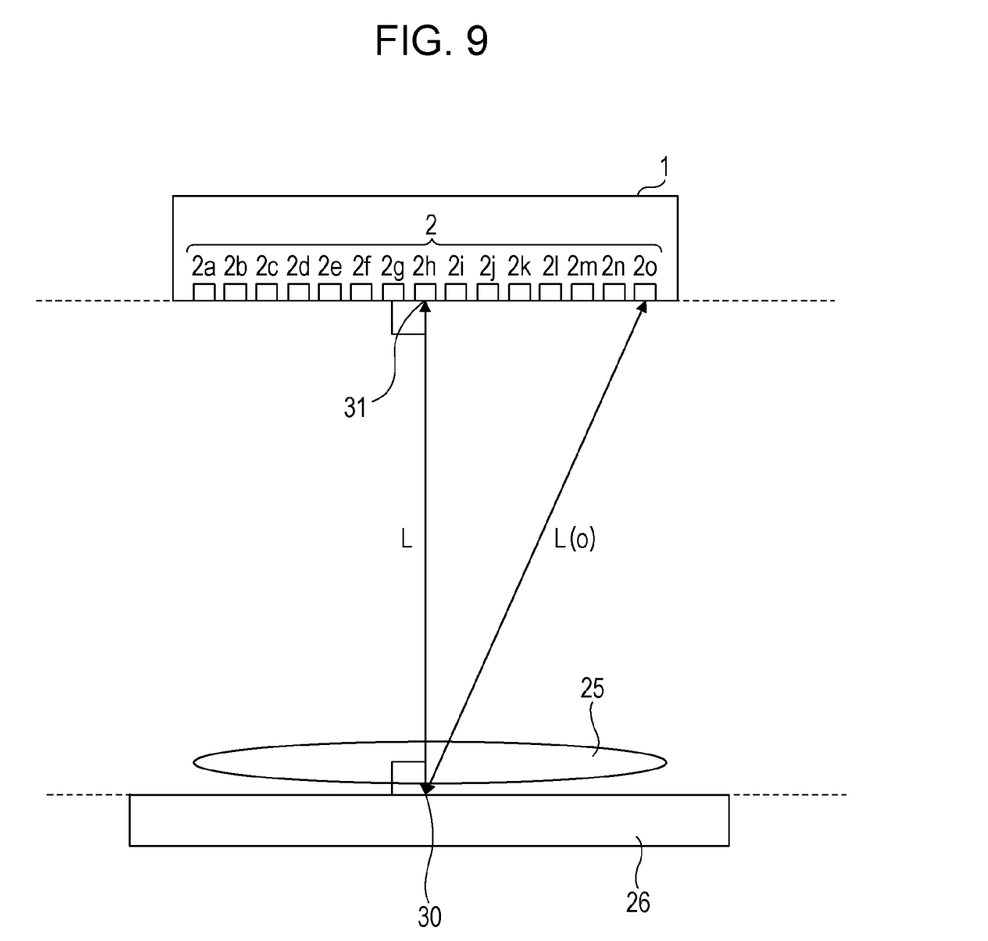
FIG. 9 is an explanatory view illustrating a method for controlling the radiographic imaging system according to the third embodiment.

A method for driving the radiation sources 2a to 2o of FIG. 9 may be the same as that of the first embodiment or the second embodiment. That is, radiographing time or an anodic current of each of the radiation sources 2a to 2o is changed depending on a distance between an arbitrary point 30 and each of the radiation sources 2a to 2o. Alternatively, both of the radiographing time and the anodic current of each of the radiation sources 2a to 2o may be changed. In the present embodiment (arrangement shown in FIG. 9), the arbitrary point 30 may be, for example, an arbitrary point on the detector 26. Alternatively, for example, the arbitrary point 30 may be set at a point of intersection of a perpendicular line passing through the central position 31 of the radiation source array 2 and the detector 26, where the detector 26 is located at a desired SID. The distance L may be set a priori based on a standardized source-to-image distance (SID) which is typically established by medical regulatory entities according to the type of imaging study to be performed. Then, the distance from each radiation source 2i, 2j, 2k, 2l, 2m, 2n, and 2o to the arbitrary point 30 are calculated as described above, based on basic trigonometry.

As described above, variation in an exposure dose at the arbitrary point 30 may be reduced by changing the radiographing time or the anodic current of each radiation source depending on the distance between the arbitrary point 30 and each of the radiation sources. In the radiographic imaging system of the present embodiment, a favorable image with less variation in the exposure dose may be obtained by aligning the radiographing center position of the sample 25 with a position as near as possible to the arbitrary point 30.

As described above, according to the present embodiment, the radiographic imaging system with improved image quality may be provided by reducing variation in the exposure dose resulting from the differences in the positions of the radiation sources.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-152180, filed Jul. 23, 2013, which is hereby incorporated by reference herein in its entirety.

What is claimed is:

1. A radiation generator comprising:
    an electron source array including a plurality of electron sources each of which is configured to emit electrons;
    a radiation source array having a plurality of radiation sources arranged in series from one array end to the other array end of the radiation source array corresponding to the electron source array; and
    a control unit configured to control each of the electron sources in the electron source array so as to form a dose distribution of radiation in the radiation source array,
    wherein the control unit controls the electron sources such that each radiation source sequentially irradiates a common region with a controlled dose of radiation controlled based on a different position of the radiation source and the dose distribution of radiation shows a decreasing profile and an increasing profile in that order from the one array end to the other array end.

2. The radiation generator according to claim 1, further comprising extraction electrodes between the electron sources and the radiation sources,
wherein the control unit sequentially selects each radiation source with potential of the radiation sources being fixed, applies an operation potential to an electron source corresponding to a selected radiation source, and provides cutoff potential to an electron source corresponding to a radiation source that is not selected.

3. The radiation generator according to claim 1, further comprising
extraction electrodes between the electron sources and the radiation sources,
wherein the control unit sequentially selects each radiation source with potential of the electron sources being fixed, applies an operation potential to an extraction electrode corresponding to a selected radiation source and provides cutoff potential to an extraction electrode corresponding to a radiation source that is not selected.

4. A radiography system comprising:
    the radiation generator according to claim 1;
    a radiation detecting device having a detection surface configured to detect radiation emitted from the radiation generator and passed through a subject; and
    a control device configured to control the radiation generator and the radiation detecting device in a coordinated manner.

5. The radiography system according to claim 4, wherein the radiography system has a tomosynthesis imaging mode in which the subject is irradiated with radiation emitted from each of the radiation sources sequentially at different angles, and a non-tomosynthesis imaging mode in which the subject is irradiated with radiation emitted only from a specific radiation source.

6. The radiography system according to claim 4,
    wherein the radiation source array forms an irradiating area on the detection surface so as to define a field of radiographing and a center of the field of radiographing, and
    wherein the control unit controls each electron source of the electron source array in each position of the radiation source so as to reduce a deviation of an exposure dose due to a geometric attenuation inversely proportional to a square of a distance between each radiation source and the center of the field of radiographing such that a common region in a subject is irradiated uniformly from each of the radiation sources.

7. The radiography system according to claim 4, wherein the radiation source array forms an irradiating area on the detection surface so as to define a field of radiographing and a center of the field of radiographing, and wherein the dose distribution of radiation controlled by the control unit shows a distribution proportional to a square of a distance between each radiation source and the center of the field of radiographing such that a common region in the subject is irradiated uniformly from each of the radiation sources.

8. The radiation generator according to claim 1, wherein the control unit controls a radiating period of each of the radiation sources.

9. The radiation generator according to claim 1, wherein the control unit controls an amount of current which flows through a target corresponding to each of the radiation sources.

10. The radiation generator according to claim 1, wherein the control unit controls each electron source of the electron source array in each position of the radiation source and is configured to reduce a deviation of exposure dose due to a geometric attenuation.

11. The radiation generator according to claim 1,
wherein the dose distribution of radiation controlled by the control unit shows a distribution proportional to a square of a distance between each radiation source and the center of the radiation source array.

12. A radiography system comprising:
a radiation generator comprising;
   an electron source array including a plurality of electron sources each of which is configured to emit electrons;
   a radiation source array having a plurality of radiation sources arranged in series from one array end to the other array end of the radiation source array corresponding to the electron source array; and
   a control unit configured to control each electron source in the electron source array so as to form a dose distribution of radiation in the radiation source array,
a radiation detecting device having a detection surface configured to detect radiation emitted from the radiation generator and passed through a subject; and
a control device configured to control the radiation generator and the radiation detecting device in a coordinated manner,
wherein the radiation source array forms an irradiating area on the detection surface so as to define a field of radiographing and a center of the field of radiographing, and
wherein the dose distribution of radiation shows an increasing profile in radiation dose in accordance with increasing a distance between each of the radiation source and the center of the field of radiographing.

13. The radiography system according to claim 12, wherein the center of the field of radiographing is defined as a point where a perpendicular line extending from the center of the radiation source array intersects the detection surface.

14. The radiography system according to claim 13, wherein the distance between each of the radiation source and the center of the field of radiographing is determined according to basic trigonometry of a triangle formed by the perpendicular line, a distance between the center of the radiation source array and each radiation source, and a line between each of the radiation source and the center of the field of radiographing.

15. The radiography system according to claim 12, wherein the control unit controls a radiating period of each of the radiation sources.

16. The radiography system according to claim 12, wherein each of the radiation sources includes a target, and
   wherein the control unit controls an amount of current that flows through the target of each of the radiation sources.

* * * * *